US00RE38268E

(19) United States
(12) Reissued Patent
Le Louarn

(10) Patent Number: US RE38,268 E
(45) Date of Reissued Patent: Oct. 7, 2003

(54) RHINOPLASTY INSTRUMENTS

(76) Inventor: Claude Le Louarn, 59, rue Spontini, F-75116 Paris (FR)

(21) Appl. No.: 10/080,027

(22) PCT Filed: Mar. 11, 1997

(86) PCT No.: PCT/FR97/00427

§ 371 (c)(1),
(2), (4) Date: Jan. 19, 1999

(87) PCT Pub. No.: WO97/33521

PCT Pub. Date: Sep. 18, 1997

Related U.S. Patent Documents

Reissue of:
(64) Patent No.: 6,264,669
Issued: Jul. 24, 2001
Appl. No.: 09/142,815
Filed: Jan. 19, 1999

(30) Foreign Application Priority Data

Mar. 11, 1996 (FR) ..... 96 03042

(51) Int. Cl.[7] ..... A61B 17/32
(52) U.S. Cl. ..... 606/174; 30/254
(58) Field of Search ..... 606/174, 175, 606/206; 30/29, 194, 196, 197, 254–260; D8/57

(56) References Cited

U.S. PATENT DOCUMENTS

| | | | | |
|---|---|---|---|---|
| 252,306 | A | 1/1882 | Ewing | 606/175 |
| 342,617 | A | 5/1886 | Ligon | 30/194 |
| 791,917 | A | 6/1905 | Koeth | 606/175 |
| 801,471 | A | 10/1905 | Miller | 606/175 |
| D53,606 | S | 7/1919 | Rauh | D8/57 |
| D143,945 | S | 2/1946 | Wolff | D8/57 |
| 2,397,823 | A | 4/1946 | Walter | 7/135 |
| D161,670 | S | 1/1951 | Abraham | D8/57 |
| 2,619,965 | A | 12/1952 | Goldstone | |
| D171,837 | S | 3/1954 | Blanchaert | D8/57 |
| 3,548,496 | A | 12/1970 | Van Hook | 7/135 |
| 3,557,792 | A | 1/1971 | Rubin | |
| 3,631,858 | A | 1/1972 | Ersek | 606/175 |
| D264,677 | S | 6/1982 | Perry, Jr. | D8/57 |
| 4,385,628 | A | 5/1983 | Straith | 606/175 |
| D278,117 | S | 3/1985 | Smith | D8/57 |
| D331,179 | S | 11/1992 | Omichi | D8/57 |
| 5,168,629 | A | 12/1992 | Willard | 30/194 |
| 5,400,452 | A | 3/1995 | Goldstein | 7/135 |
| D363,122 | S | 10/1995 | Uetake | D8/57 |
| 5,486,185 | A | 1/1996 | Freitas et al. | 606/206 |

FOREIGN PATENT DOCUMENTS

| | | |
|---|---|---|
| DE | 2928689 | 2/1981 |
| DE | 2928689 A | 2/1981 |
| GB | 8357 | 8/1910 |
| GB | 2169 | 3/1911 |

*Primary Examiner*—David O. Reip
(74) *Attorney, Agent, or Firm*—McDonnell Boehnen Hulbert & Berghoff

(57) ABSTRACT

Instruments including a pair of scissors (1) for removing the bump from an aquiline nose, wherein the scissors have cutting blades (5,6), with mutually facing concave cutting edges (7,8) matching the shape of the bump, as well as a clamp with two cutting blades each having a double curvature in two perpendicular planes so that the clamp fits the lateral bones of the nose. The clamp enables lateral osteotomy of the nose once the bump has been removed by means of the scissors (1), whereby the surgeon can reconstruct the shape and profile of the nose. The number of instruments needed may thus be reduced considerably relative to the prior art, while the reliability, accuracy and safety of the operation may be substantially enhanced.

10 Claims, 5 Drawing Sheets

RHINOPLASTY INSTRUMENTS

Matter enclosed in heavy brackets [ ] appears in the original patent but forms no part of this reissue specification; matter printed in italics indicates the additions made by reissue.

The present invention relates to instrumentation for plastic surgery of the nose, for modifying the shape of the latter (rhinoplasty), more particularly for removing an osseocartilaginous bulge from the nose and for performing lateral osteotomy of the nasal bones.

As is known, beneath the skin of the nose there is the nasal bone, extending from the halfway point of the nose to the forehead, and then the cartilage, which extends from the halfway point of the nose to the tip of the nose, the bone and the cartilage are held between the skin on the outside and the nasal mucous membrane on the inside. The septum is the cartilage which supports this arch in the centre.

The nasal bulge thus consists of an oseous half and a cartilaginous half. To perform its ablation, so as to give the nose the desired appearance, with smooth profile, the following procedure has hitherto been followed.

These two halves of the bulge (bone and cartilage) are sectioned using two different types of instruments:

a) For the cartilage, use is made of scissors whose action is halted consequently at the bone. For the bone, use is made of a straight chisel and a hammer, with which the chisel is advanced in order to remove the remaining osseous part of the nasal bulge.

Unfortunately, this technique has the disadvantage that it does not in practice prevent variations in cutting angles between the two tools. These angular deviations remain visible on the nose profiles which are obtained, even when these are considered satisfactory. For example, there may still be more bone volume on the profile compared to the line of the cartilage profile.

Once the bulge has been removed, the two bones of the nose must be brought together to reconstruct a nose of normal width. To do this, the surgeon performs lateral osteotomy of the nose, that is to say a cut from the base of the two lateral bones, in order to bring together their upper margins. This cut is made using a straight chisel and hammer, with two variations in axes, namely a variation in the horizontal plane (the patient being assumed to be lying on a horizontal plane) and a variation in axis in the frontal plane.

These two lateral osteotomies are difficult to perform in a satisfactory manner, so that the point of arrival of these cuts is not always situated at the intended location. In addition, the bone may fragment because of the variations in axes given to the chisel, which the bone does not accept. Finally, although the following is uncommon, the chisel may slip as far as the eye and cause an eye wound.

A saw is more rarely used for these lateral osteotomies. Because the cut is straight, and not curved, its angle of attack is difficult to control, and the handling of the chisel or saw is not easy. Finally, a height of bone equal to the height of the blade (2 mm) disappears. This procedure thus presents real difficulties and the result obtained is not perfect.

Finally, these known techniques necessitate the use of several different tools; in particular, the first operation, intended to remove the nasal bulge, requires two tools, or even three, including the hammer associated with the straight chisel.

The object of the invention is therefore to provide instrumentation which permits more satisfactory results, which is less difficult to use and which is also less expensive than the instrumentation used hitherto.

According to the invention, the instrumentation for plastic surgery of the nose comprises:

a pair of scissors intended to remove the bulge and having cutting blades with concave edges which face each other and are adapted to the anatomy of the bulge, and forceps, with two cutting blades each having at least one curvature in one of two perpendicular planes, and adapted to the anatomy of the lateral bones of the nose.

Thus, the pair of scissors alone allows the cartilaginous and osseous parts of the bulge to be removed in a single operation and therefore replaces the three tools mentioned above.

Likewise, the forceps replace the straight chisel and the hammer, while making it possible to perform much less difficult and more satisfactory lateral cuts than the cuts performed hitherto.

According to one feature of the invention, the end of one of the cutting blades of the pair of scissors is provided with a transverse stud directed towards the end of the second blade.

This stud can either bear on the upper end of the bridge of the nose or be embedded in one of the lateral bones of the nose in order to correctly fix the positioning of the scissors prior to cutting.

The blades and cutting edges of the scissors can also have a curvature in a plane perpendicular to the general plane of the pair of scissors.

According to another characteristic of the invention, one of the blades of the osteotomy forceps has a concave cutting edge, while the second blade is provided with a convex edge.

Other features and advantages of the invention will become clear from the following description in which reference is made to the attached drawings which illustrate one embodiment thereof by way of a non-limiting example.

Figure 1:
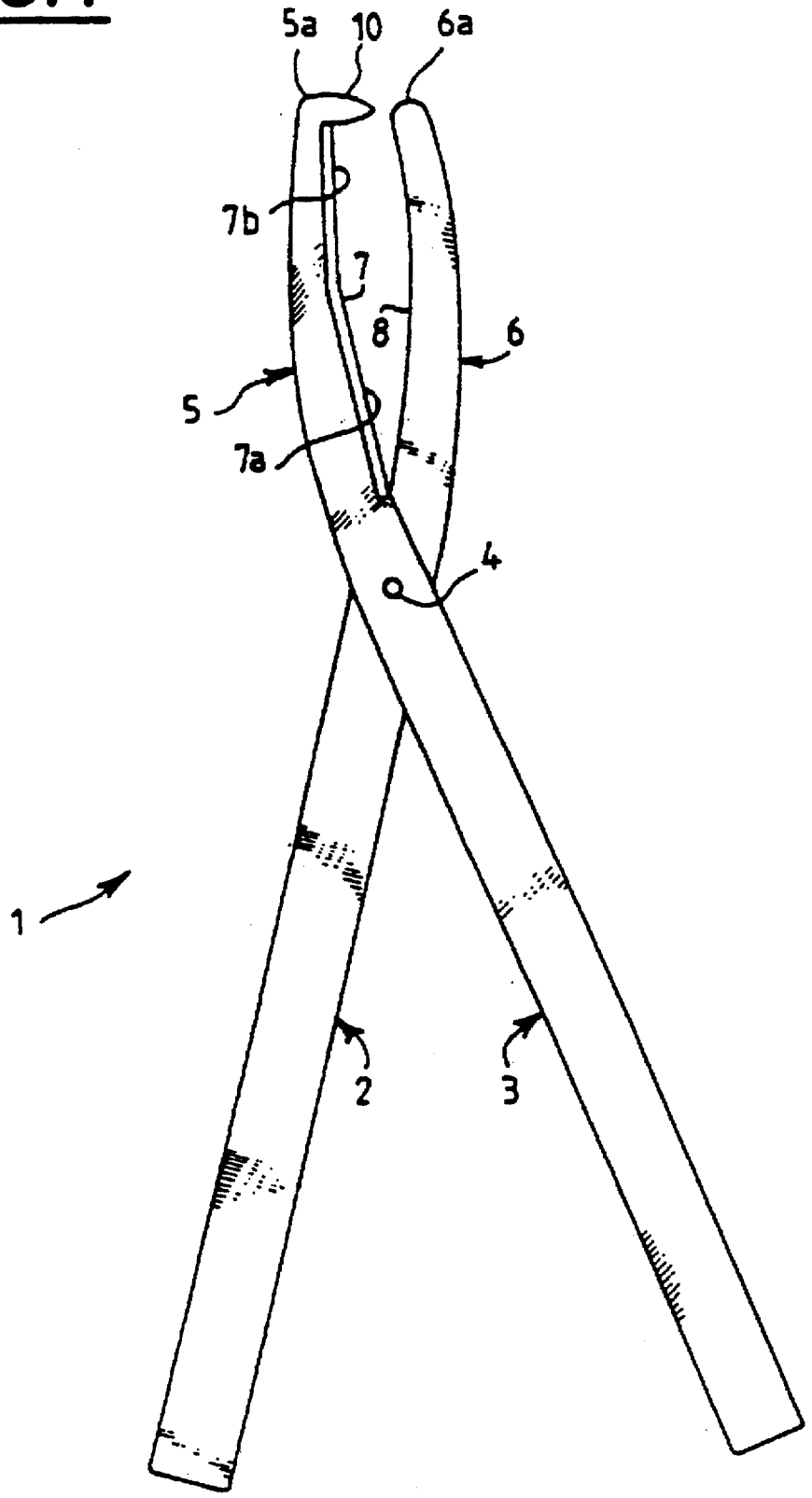
FIG. 1 is a plan view, substantially to scale, of one embodiment of the pair of scissors for ablation of the nasal bulge.

The instrumentation for plastic surgery of the nose illustrated in the drawings comprise a pair of scissors (FIGS. 1 to 3) and forceps 18 with cutting blades (FIGS. 5 to 7) adapted respectively for each of the two rhinoplasty operations set out hereinabove.

The scissors 1 comprise two handles 2, 3 which are articulated about a pin 4 and whose ends constitute respective cutting blades 5, 6 with facing concave cutting edges 7, 8 which are adapted to the anatomy of a bulge 9 on the nose 11 of a patient P, which bulge 9 is to removed. The bulge 9 is made up of a cartilaginous part 9a and an osseous part 9b.

The cutting edge 7 of the blade 5 is advantageously made up of two rectilinear sections 7a, 7b extending in a slightly concave general direction. The section 7b, farthest from the hinge pin 4, can be continued, as shown by a transverse stud 10 which is directed towards the rounded end 6a of the second blade 6 and is connected via a rounded end 5a to the rest of the blade 5.

The cutting edge 8 of the blade 6 forms a regular concavity facing the concave edge 7 and substantially along the same length. Of course, the geometry of the cutting edges 7, 8 can vary considerably compared to that represented in the drawings, while remaining adapted to the particular anatomy of the person to be operated on. For example, the two scissors 7a, 7b can be replaced by a concave circular section.

By virtue of this arrangement of the scissors 1 and their concave curved cutting blades 5, 6, the cartilaginous part 9a and the osseous part 9b of the nasal bulge 9 can be sectioned in a single operation, without variation in the cutting axis between the osseous part 9b and the cartilaginous part 9a. Of course, the surgeon chooses, from a set of scissors 1 of different dimensions, those scissors which are best adapted to be anatomy of the nose of the person from which the bulge 9 is to be removed. In other words, the space between the two edges 7, 8 prior to cutting is determined by the shape of the nose 11 of the patient P at the location where the section is to be performed.

The latter can be done in two different ways.

Figure 2:
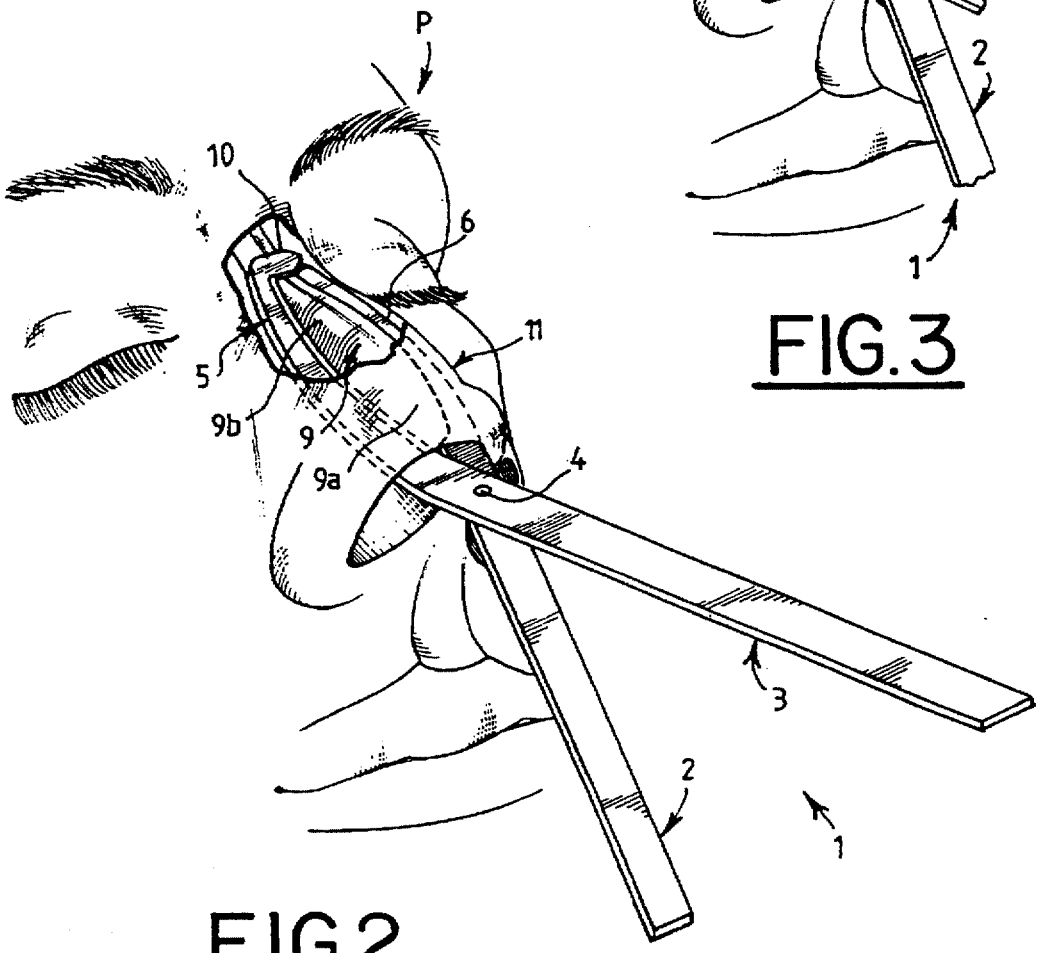
FIG. 2 is a perspective view illustrating a first way of using the pair of scissors from FIG. 1 on a patient's nose, for the purpose of removing the bulge.

Thus, in FIG. 2, the stud 10 is placed bearing on the nasal bridge at the base of the bulge 9, level with the eyes of the patient P, and determines the location where the cut is to stop. The surgeon introduces the ends 5a, 6a of the blades 5, 6 into one of the nostrils of the patient, namely the right nostril for a right-handed surgeon (FIG. 2), with the branches 5 and 6 under the skin of the nose and against the bone and the cartilage.

The fact that the ends 5a, 6a are rounded makes it easier to insert the blades 5, 6 through the nostrils. This is done until the stud 10 comes to bear on the upper base of the bulge 9 at the intended location. The surgeon then simultaneously cuts the parts 9a and 9b of the bulge 9.

Figure 3:
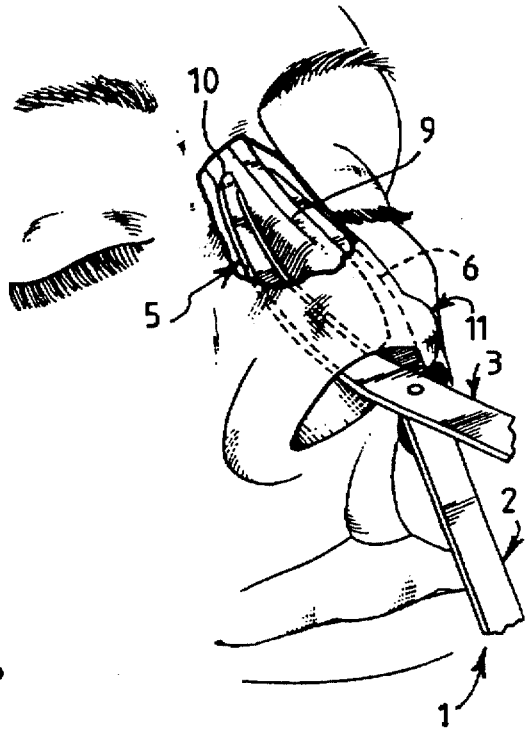
FIG. 3 is a perspective view, with part cut away, illustrating a second way of using the pair of scissors from FIG. 1 for removing the bulge.

It is possible to proceed in the manner illustrated in FIG. 3: having introduced the ends of the blades 5, 6 into the right nostril of the nose 11, as was explained above, the surgeon drives the stud 9 into the actual bone of the nose at the intended location of the end of the cut, that is to say to the point where the nasofrontal angle is to be cut. Under these conditions, the cut can be made without any risk of the blades 5, 6 slipping in relation to the intended positioning, which fact affords greater safety of the intervention.

Once the cut has been made, the blades 5, 6 are withdrawn from the nose 11 and the bulge 9 extracted via the nostril.

The pair of scissors 1 which has just been described in open to various alternative embodiments. Thus, as has already been indicated, the scissors, while still retaining the principle of scissors with curved blades, can have different shapes and dimensions on the basis of several elements, in particular the volume of the bulge on the patient and the solidity of the bone. Likewise, the stud 10 can be omitted, and at least one of the cutting edges 7, 8 can be equipped with micro teeth 30, which present the blades from slipping on the nasal bone.

Figure 4:
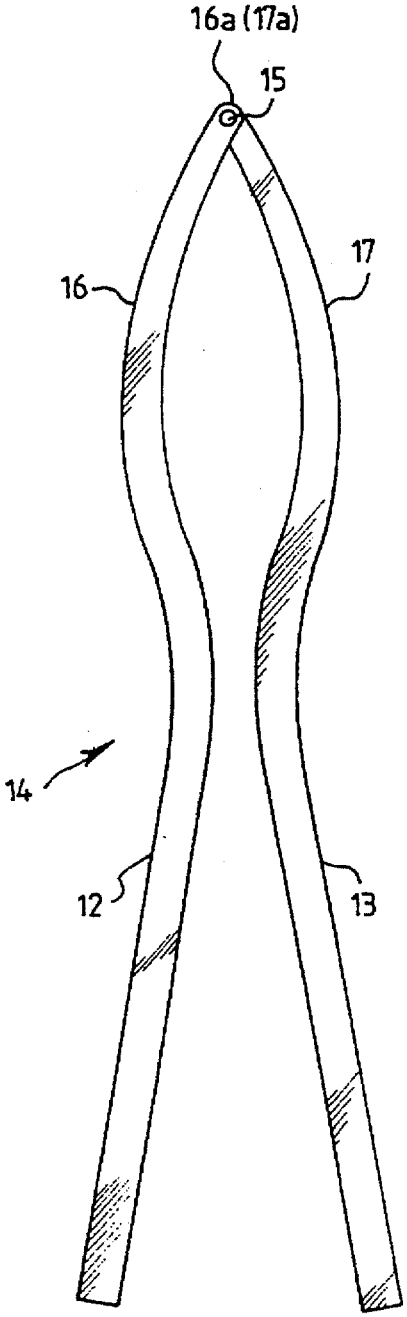
FIG. 4 is a plan view, substantially to scale, of a second embodiment of the pair of scissors in FIG. 1.

Another possible variant is illustrated is FIG. 4: in this, the handles 12, 13 of the scissors 14 are articulated on a pin 15 at the free founded ends 16a, 17a of their cutting blades 16, 17. When the scissors 14 are used, the axis of rotation 15 is arranged at the nasofrontal angle.

According to another possible alternative embodiment, the blades 5, 6 or 16, 17 can have a slight curvature in a vertical plane, that is to say in a plane perpendicular to the plane of FIGS. 1 and 4, in order to obtain a slightly concave line of profile of the bridge of the nose.

However, in all cases the concave shape of the cutting blades and of their edges in the general plane of the scissors is necessary in order to be able to adapt to the osseocartilaginous shape of the bulge 11 to be removed.

The fact that the free ends (5a, 6a; 16a, 17a) of the cutting blades 5, 6, 16, 17 are rounded makes it possible to avoid weakening the skin of the nose, as happens with the usual straight chisels, such as those used in the prior art.

The rhinoplasty instrumentation proposed by the invention also comprises forceps 18 (FIGS. 5 to 7) adapted for lateral osteotomy of the nasal bones, after cutting the bulge 11, in order to bring together the two lateral parts of the nose 11.

The forceps 18 are made up of two handles 19, 21 which are articulated about a pin 22 and are provided with respective cutting blades 23, 24 having the respective edges 25, 26.

Figure 5:
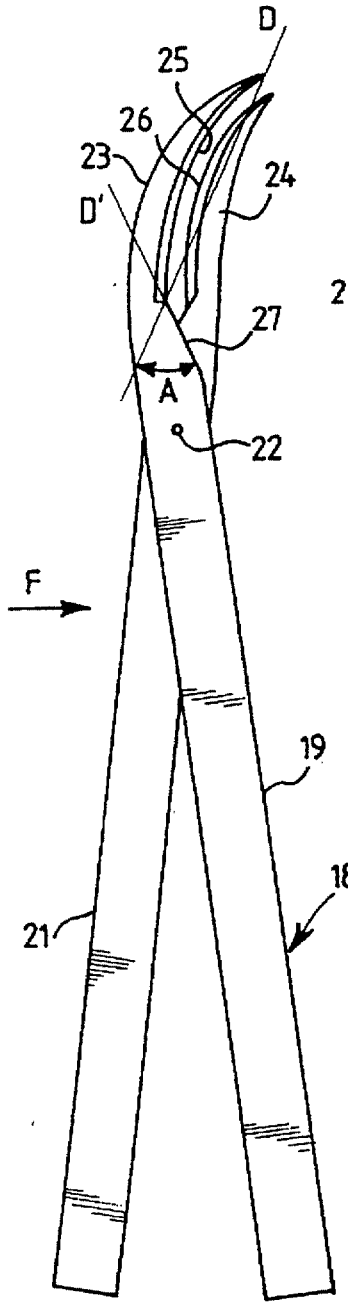
FIG. 5 is a plan view, substantially to scale, of forceps with cutting blades, adapted for the lateral osteotomy of the nose after removal of the bulge.
Figure 6:
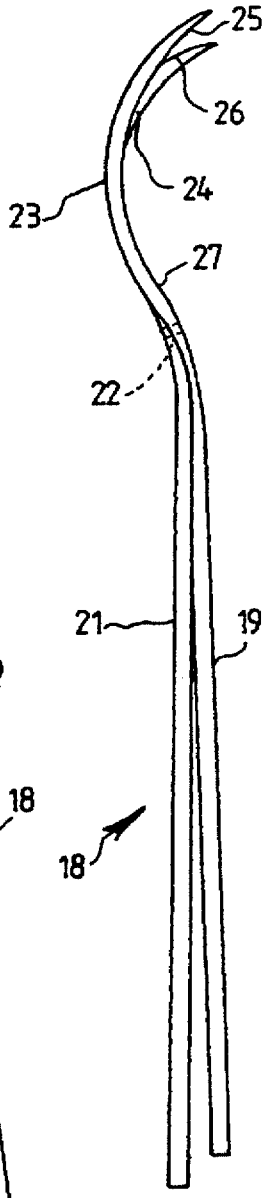
FIG. 6 is a longitudinal elevation view according to the arrow F of the forceps in FIG. 5.

The blades 23, 24 and their edges 25, 26 each have a double curvature in two perpendicular planes, namely the horizontal plane and the vertical plane, the cutting edge 25 additionally being concave while the associated cutting edge 26 is convex. FIG. 5 shows the curvature of the blades 23 and of their edges 25, 26 in the horizontal plane, while their respective curvatures in the vertical plane are illustrated in FIGS. 6. As the curvatures of the cutting edges 25, 26 are adapted to the shape of the actual bone of the nose, right forceps and left forceps are therefore necessary.

Each cutting blade 23, 24 has a rectilinear part 27 between its axis of articulation 22 on the other blade and the incurved part constituting the cutting edge 25, 26; a straight line D passing through the ends of the incurred part 25 or 26 forms, with a straight line D' passing through the rectilinear part 27, an angle A of between 5 and 90°.

As with the scissors 1, the cutting edges 25, 26 can be equipped with micro teeth (not shown). According to an advantageous variant (FIG. 8), the free ends of the blades 23, 24 can be equipped with a flat point 28 formed by a disc arranged in the continuation of the corresponding cutting edge 25 or 26. The disc 28 can either be attached to the point of the cutting blade or can be made in one piece with the latter.

Figures 7, 8:
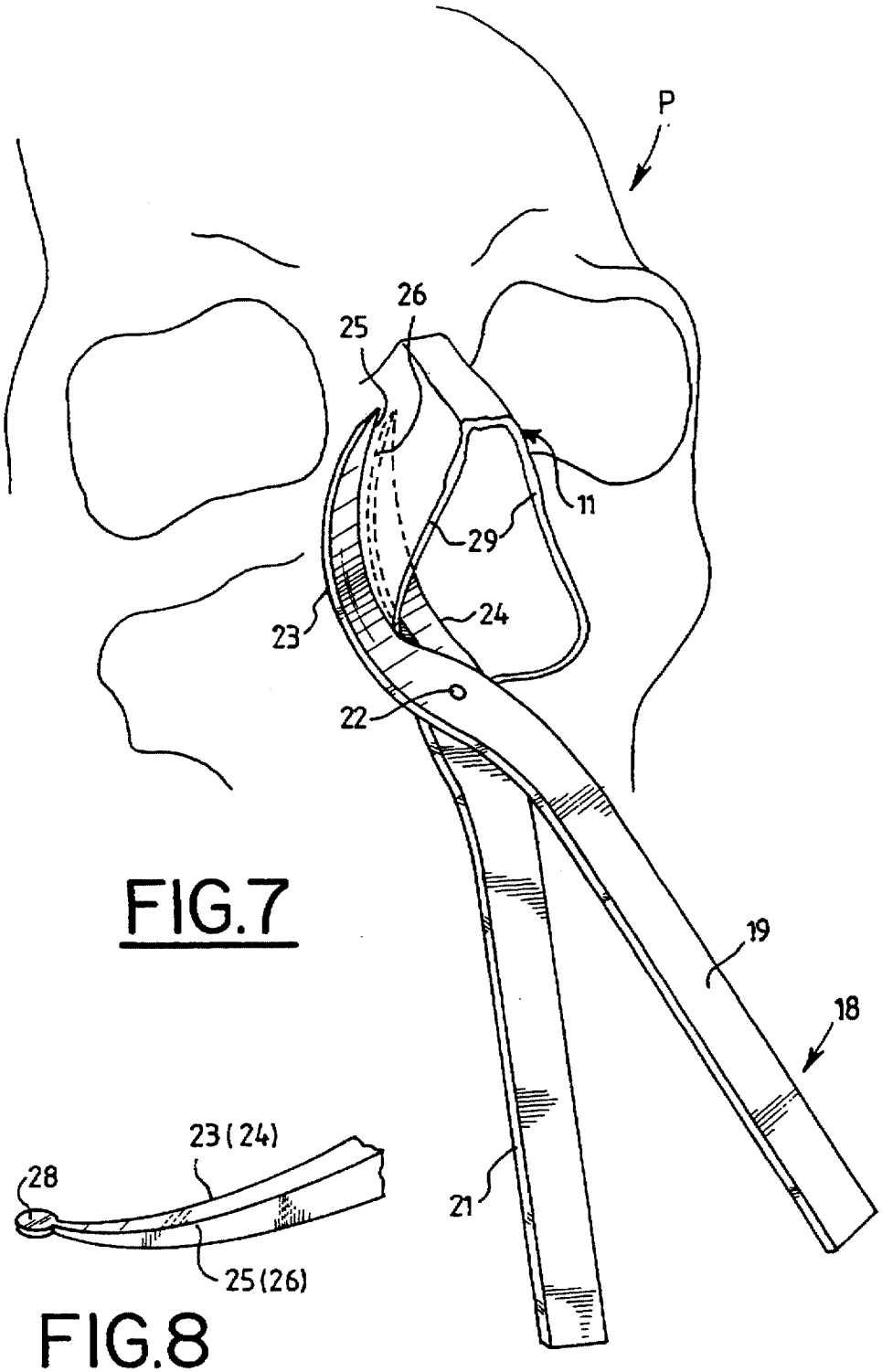
FIG. 7 is a perspective view illustrating the use of the forceps in FIGS. 5 and 6 for lateral osteotomy of a patient's nose after removal of the bulge.
FIG. 8 is a partial perspective view of a variant embodiment of the forceps in FIGS. 5 to 7.
Figure 9:
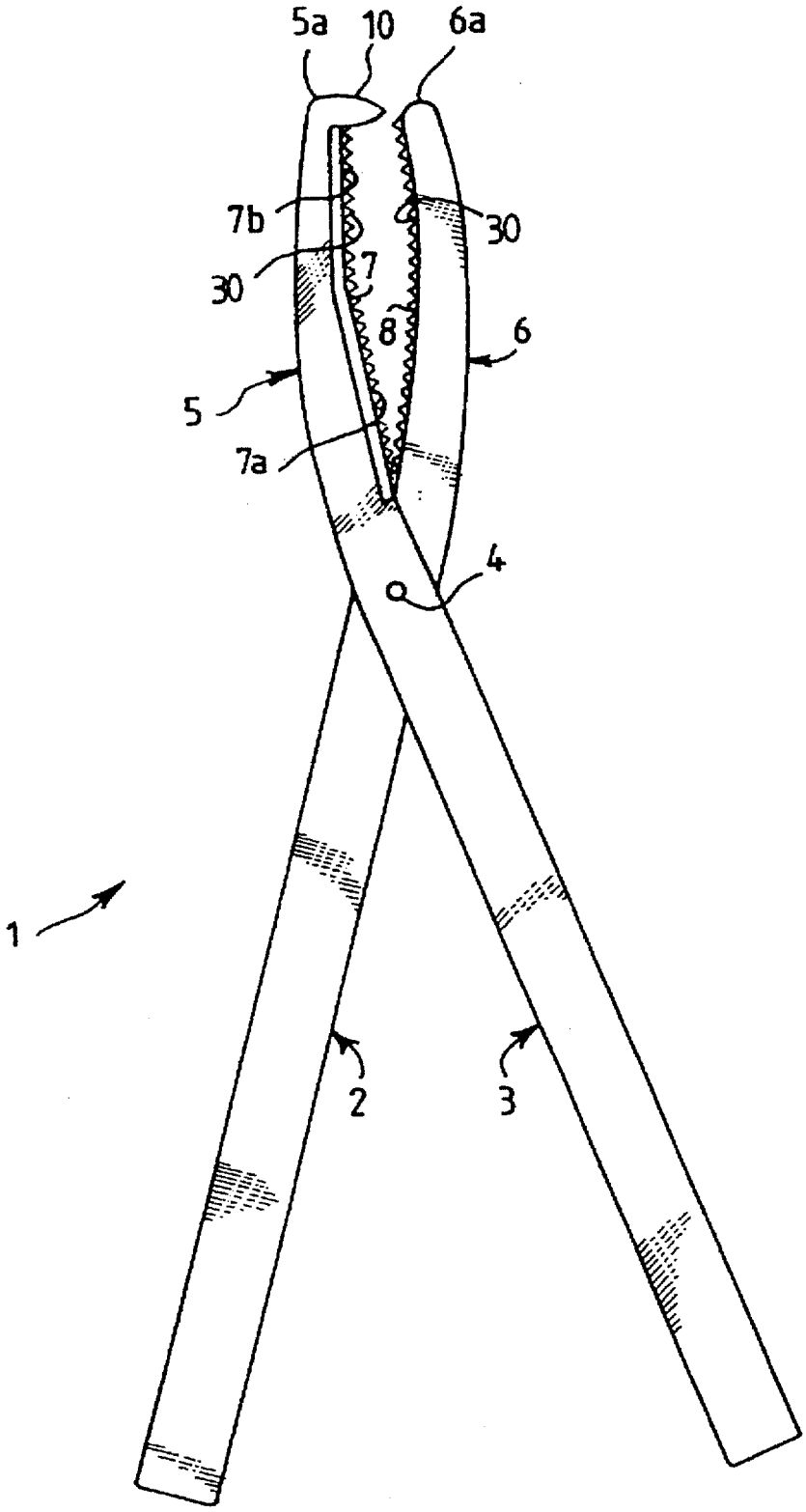
FIG. 9 is a plan view of a variant embodiment of the scissors of FIG. 1.

The advantage of the abovementioned angular range relating to the straight lines D and D' lies in the fact that it makes it possible to arrange the blades 23, 24 almost in parallel in order to slide them almost parallel to the bone when the instrument 18 is placed against the lateral bone 29 of the nose (FIG. 7). The outer blade 23 is introduced between the skin and the bone, and the inner blade 24 is slid between the bone and the mucous membrane.

The cutting operation is performed on each lateral bone using the corresponding forceps. However, it is possible to produce forceps with a single curvature of the blades 23, 24 in one or other of the abovementioned perpendicular planes, which then makes it possible to use the same forceps for the right and left sides of the nose.

The possible arrangement of one or two flat end discs 28 on the cutting blades makes it easier to introduce the latter between the skin and the bone on the one hand, and between the bone and the mucous membrane on the other hand, by promoting the detachment of the soft tissue in contact with the bone.

Following osteotomy of the two lateral bones of the nose using forceps such as 18, the surgeon is able to reconstruct the profile of the nose by displacing the sectioned lateral parts of the nose to the desired level in order to recomplete the nose from the front.

These instruments permit to avoid performing the rhinoplasty intervention by means of a hammer and osteotomes. Only cutting forceps or scissors are used.

What is claimed is:

1. Instrumentation kit for plastic surgery of the nose comprising:

a pair of scissors for removing an osseocartilaginous bulge from the nose, the pair of scissors having a pair of cutting blades with concave cutting edges which face each other and further having a shape that corresponds to the anatomy of the bulge, each cutting blade of said pair of cutting blades having a distal end, the pair of scissors lying in a horizontal plane;

and a cutting tool for performing lateral osteotomy of the nasal bones, the cutting tool having two cutting blades, each cutting blade of the cutting tool having a distal end, at least one curvature in one of the horizontal plane and a vertical plane, each cutting blade of the cutting tool having a shape that corresponds to the anatomy of the lateral bones of the nose.

2. Instrumentation kit according to claim 1, wherein the distal end of one of the cutting blades of the pair of scissors is provided with a transverse stud directed towards the distal end of the other cutting blade of the pair of scissors.

3. Instrumentation kit according to claim 1, wherein the cutting edges of the cutting blades of the pair of scissors are equipped with microteeth.

4. Instrumentation kit according to claim 1, wherein the cutting blades and the cutting edges of the pair of scissors have a curvature in a vertical plane, the vertical plane being perpendicular to the horizontal plane in which the pair of scissors lie.

5. Instrumentation kit according to claim 1, wherein the pair of scissors further comprises two handles, the handles being articulated via the distal ends of their respective cutting blades.

6. Instrumentation kit according to claim 1, wherein the distal ends of the cutting blades of the pair of scissors are rounded.

7. Instrumentation kit according to claim 6, wherein the distal ends of the cutting blades of the cutting tool are equipped with a flat disc along the respective cutting edge.

8. Instrumentation kit according to claim 1, wherein one of the cutting blades of the cutting tool has a concave cutting edge, while the other cutting blade of the cutting tool is provided with a convex cutting edge.

9. Instrumentation kit according to claim 8, wherein each cutting blade of the cutting tool has a rectilinear part between its axis of articulation with the other cutting blade of the cutting tool and an incurved part forming the cutting edge, and wherein an angle A of between 5 and 90 degrees is formed by the intersection of a first straight line passing through the ends of the incurved part in a second straight line passing through the rectilinear part.

10. Instrumentation kit according to claims 8 to 7, wherein at least one of the cutting edges of the cutting blades of the cutting tool is equipped with microtech.

* * * * *